United States Patent [19]
Johnson

[11] Patent Number: 5,266,928
[45] Date of Patent: Nov. 30, 1993

[54] WET DIAPER DETECTOR

[76] Inventor: Lonnie G. Johnson, 4030 Ridgehurst Dr., Smyrna, Ga. 30080

[21] Appl. No.: 890,162

[22] Filed: May 29, 1992

[51] Int. Cl.[5] .............................................. G08B 21/00
[52] U.S. Cl. .................................. 340/604; 340/573; 128/886; 604/361
[58] Field of Search ............... 340/603, 604, 605, 573; 200/61.04, 61.05; 128/886; 604/361

[56] References Cited

U.S. PATENT DOCUMENTS

| | | | |
|---|---|---|---|
| 2,127,538 | 8/1938 | Seiger | 200/61.05 |
| 3,460,123 | 8/1969 | Bass | 340/573 |
| 3,809,078 | 5/1974 | Mozes | 128/886 |
| 4,106,001 | 8/1978 | Mahoney | 340/604 |
| 4,205,672 | 6/1980 | Dvorak | 128/886 |
| 4,356,818 | 11/1982 | Macias et al. | 128/886 |
| 4,484,573 | 11/1984 | Yoo | 128/886 |
| 4,539,559 | 9/1985 | Kelly et al. | 340/573 |
| 4,653,491 | 3/1987 | Okada et al. | 128/886 |
| 4,704,108 | 1/1987 | Okada et al. | 604/361 |
| 4,738,260 | 4/1988 | Brown | 128/886 |
| 4,796,014 | 1/1989 | Chia | 340/573 |
| 5,036,859 | 8/1991 | Brown | 128/886 X |

Primary Examiner—Jeffrey Hofsass
Attorney, Agent, or Firm—Hopkins & Thomas

[57] ABSTRACT

A wet diaper detector comprises an elongated strip of material sized to be positioned in a diaper with a portion of the strip residing in a region of the diaper subject to wetness and an end of the strip protruding from the diaper at the upper rear or front portion thereof. The strip carries a pair of spaced conductors that extend along the length of the strip and terminate at the protruding end thereof. A detector and alarm assembly is adapted to be releasably coupled to the protruding end of the elongated strip and is configured to monitor the electrical resistance between the spaced conductors of the strip. When the diaper is wet by its wearer, the resistance between the spaced conductors of the strips falls below a pre-established value whereupon the detector activates the alarm to alert an attendant to change the diaper. When the diaper is changed, the detector and alarm assembly is decoupled from the strip for reuse and the strip is discarded along with the soiled diaper.

4 Claims, 3 Drawing Sheets

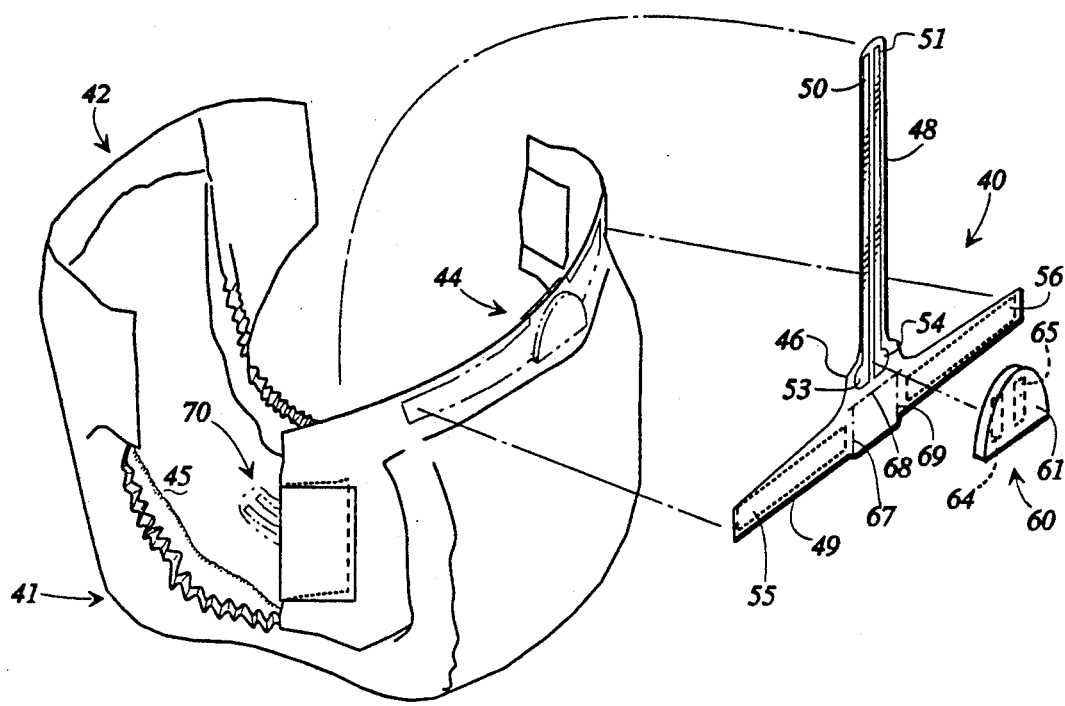
*FIG 4*
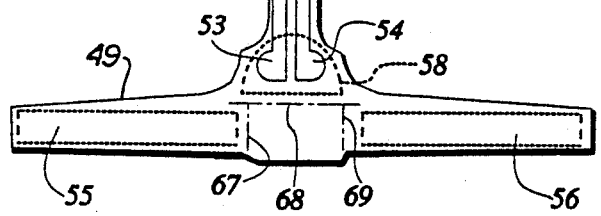
*FIG 5*          *FIG 6*

WET DIAPER DETECTOR

FIELD OF THE INVENTION

This invention relates generally to moisture sensing devices and more particularly to a wet diaper detector assembly for alerting parents or attendants to the presence of wetness in an infant's diapers or undergarments.

BACKGROUND OF THE INVENTION

Baby diaper rash is for the nursing mother one of the most enigmatic problems of infant rearing. One of the primary causes of such diaper rash is, of course, that babies frequently wet their diapers and wear the wet diapers for prolonged periods before they are changed. While a few babies tend to cry when wet, many babies do not cry, and the mothers of this latter group of babies are not alerted to the wet diaper condition until the diaper has been worn for a time sufficient to cause diaper rash.

In an effort to reduce the time during which wet diapers are in contact with a baby's skin, mothers often adhere to a specific change of diaper schedule wherein a baby's diapers are changed periodically according to a pre-established timetable. Although such diaper-changing schedules are helpful, a real reduction of time during which urine contacts the baby's skin is not often realized because no prescribed time table can anticipate an individual baby's changeable physical constitution. For example, an infant might wet its diaper immediately after a scheduled change of the diaper and thus, unknown to the mother, be left in a soiled diaper until the next scheduled change of the diaper.

Alarm devices have previously been proposed as a means for informing a parent or attendant that a wet diaper condition has occurred so that the baby's clothing can be changed and its skin cleansed to eliminate the urine/skin contact and reduce the chances of diaper rash. One example of such a proposed alarm device is disclosed in U.S. Pat. No. 3,460,123 of Bass. Bass shows a wet garment alarm system that includes a transmitter for producing a radio signal and a diaper formed with a pair of spaced conductive screens having an electrolyte disposed therebetween. The transmitter is electrically coupled to the screens and adapted to produce a radio signal when the resistance between the screens falls below a predetermined level.

In use, the transmitter of Bass is secured to the upper waist portion of an infant's diaper, and the diaper is secured to its wearer with the pair of conductive screens positioned at the crotch portion of the diaper. When the diaper is wet by the wearer, urine flows into the crotch portion of the diaper and electrically bridges the space between the conductive screens thus reducing the resistance between the screens. This reduced resistance, in turn, actuates the transmitter to produce a radio signal for activating a remote alarm to alert a parent or attendant to the wet diaper condition.

Another system for detecting and signaling a wet diaper condition is disclosed in U.S. Pat. No. 4,106,001 of Mahoney, wherein a garment clip houses a moisture detector and alarm. The garment clip is adapted to be clipped onto an exposed edge of a diaper or other garment to be monitored. An elongated strip of material is connected at one end to the clip and is sized to be positioned in a region of the diaper subject to wetness such as, for example, the crotch region. The strip of material includes a pair of embedded spaced electrodes that are coupled to the detector/alarm. When moisture is provided by the wearer of the undergarment, a partial short circuit occurs between the electrodes at some point along the strip of material. This short circuit is detected by the moisture detector, which activates the alarm to provide an audible indication of urination by the infant or wearer.

A similar system is disclosed in U.S. Pat. No. 4,796,014 of Chia, wherein a safety pin with spaced electrical conductors is coupled to a detector and alarm device attached to a diaper. When urine bridges the space between the electrical conductors of the safety pin, a detection circuit is completed, which, in turn, activates the alarm. The Chia device further includes a time delay circuit to ensure that the alarm does not interfere with an infant's normal urination cycle.

While these and similar devices have been somewhat successful in signaling a wet diaper condition, they still tend to exhibit numerous problems and shortcomings inherent in their respective designs. For instance, several of these devices include a pair of conductive electrodes built into the material forming the diaper itself. Such a configuration is shown in the patent of Bass. Obviously, manufacture of these types of diapers can be relatively expensive since special diaper forming machinery must be developed and implemented. Another common problem with prior art devices is that the detecting strips that reside in the diaper are configured as integral non-detachable elements of the detector and alarm circuits. With such a configuration, the entire device often must be discarded when the sensing strip becomes worn, which is inefficient and wasteful. Also, manufacturing the detection devices and alarms in some prior art devices can become complicated and costly.

Accordingly, there exists a continuing and heretofore unaddressed need for a wet diaper detector and alarm system that is usable with a conventional disposable or non-disposable diaper, is inexpensive to produce, easy and convenient to use, includes a detachable and separately disposable detector strip, and that does not require expensive and bulky housings that must be secured to a wearer's garments. It is to the provision of such a wet diaper detector and alarm system that the present invention is primarily directed.

SUMMARY OF THE INVENTION

Briefly described, the present invention comprises a wet diaper detector and alarm system for use with conventional undergarments or diapers to alert a parent or attendant to a wet diaper condition and also to provide a dependable manner by which young children can be toilet trained. In one preferred embodiment, the wet diaper detector and alarm system of this invention comprises an elongated strip of generally absorbent material having a pair of spaced embedded conductors extending therealong. The conductor bearing strip is sized to be positioned and secured in a diaper extending through a wetness prone region thereof with one end of the strip protruding from the diaper, preferably at the front or rear waistband portion thereof.

A generally rectangular flexible band supports miniaturized electronic detection and alarm circuitry and is configured to be removably attached to the protruding end of a conductor bearing strip that previously has been secured in the diaper. The band includes a pair of electrical contacts that are coupled to the detection circuit of the band with each contact being configured to become electrically coupled to a respective one of the conductors of the elongated strip when the band is attached to the strip end. With the band thus attached to the protruding end of a conductor bearing strip, the band and strip end can be removably mounted to the exterior of the diaper with a rectangular adhesive backed patch that covers and protects the band during use.

The detector of the present invention is configured to monitor the resistance between the spaced conductors of an attached conductor bearing strip and to trigger the alarm, which preferably emits a pleasant audible melody, when such resistance falls below a pre-established threshold. When the system is properly secured to an infant's diaper as described above, the electrical resistance between the two electrical conductors of the elongated strip normally remains above the pre-established threshold when the diaper is dry. However, when the wearer wets its diaper, the resulting moisture permeates the strip therein and causes the resistance between the two conductors of the strip to fall below the pre-established threshold. As a result, the detector triggers the audible alarm to alert an adult or attendant immediately of the wet diaper condition so that the diaper can be changed.

In another embodiment of the invention, a T-shaped strip of material is adapted to be secured to a diaper with its shorter leg positioned on the outside of the diaper at the upper front or rear portion thereof and with its longer leg extending therefrom into the diaper and through the crotch area thereof. A pair of spaced conductors are disposed along the length of the longer leg and each conductor terminates in a contact at the intersection of the legs of the T-shaped strip, which normally lies on the outside of the diaper. A miniaturized detector and alarm circuit is contained within a small plastic housing having a pair of spaced external contacts positioned to engage the contacts at the strip intersection when the housing is located on the T-shaped strip at the intersection of its legs.

In use, the T-shaped strip of this embodiment is placed in a diaper as described and the detector/alarm housing is positioned at the intersection of the strip's legs with its contacts engaging the contacts of the strip. The shorter leg of the T-shaped strip, which preferably bears adhesive, is then folded up and over the housing and adhesively attached to the front of the diaper to secure the detector in place. The circuitry then functions in the same way as with the previously described embodiment to signal a wet diaper condition. When a wet diaper is changed, the small detector housing is simply removed and reused while the used, inexpensive T-shaped strip is discarded with the soiled diaper.

Thus, it is seen that an improved wet diaper detector and alarm system is now provided for detecting and signaling a wet diaper condition quickly, reliably, economically, and conveniently. The components of the system are designed so that the more expensive elements, i.e. the electronic detection and alarm circuitry, are easily removed and reused while the inexpensive conductive strip, which becomes soiled along with the diaper, is simply discarded. The system is thus highly efficient relative to prior art systems.

The present invention provides great advantages in the care of wetting infants since it allows a wet diaper to be changed immediately, thus reducing greatly instances of urine induced diaper rash. The system is further advantageous in the toilet training of infants since its alarm can signal a parent or attendant to take the infant to a toilet immediately upon commencement of wetting. In this way, the child makes the mental connection between wetting and the toilet much quicker than with older fashioned toilet training techniques. These and other features, objects and advantages of the invention will become more apparent upon review of the following detailed description taken in conjunction with the accompanying drawings.

BRIEF DESCRIPTION OF THE DRAWINGS

FIG. 4 is a perspective partially exploded view showing an alternate embodiment of the wet diaper detector of the present invention.

FIG. 5 is a top plan view of the disposable T-shaped strip of the embodiment shown in FIG. 4.

FIG. 6 is a rear view showing a preferred configuration of the detector and alarm module of the embodiment shown in FIG. 4.

DETAILED DESCRIPTION OF THE PREFERRED EMBODIMENTS

Figure 1:
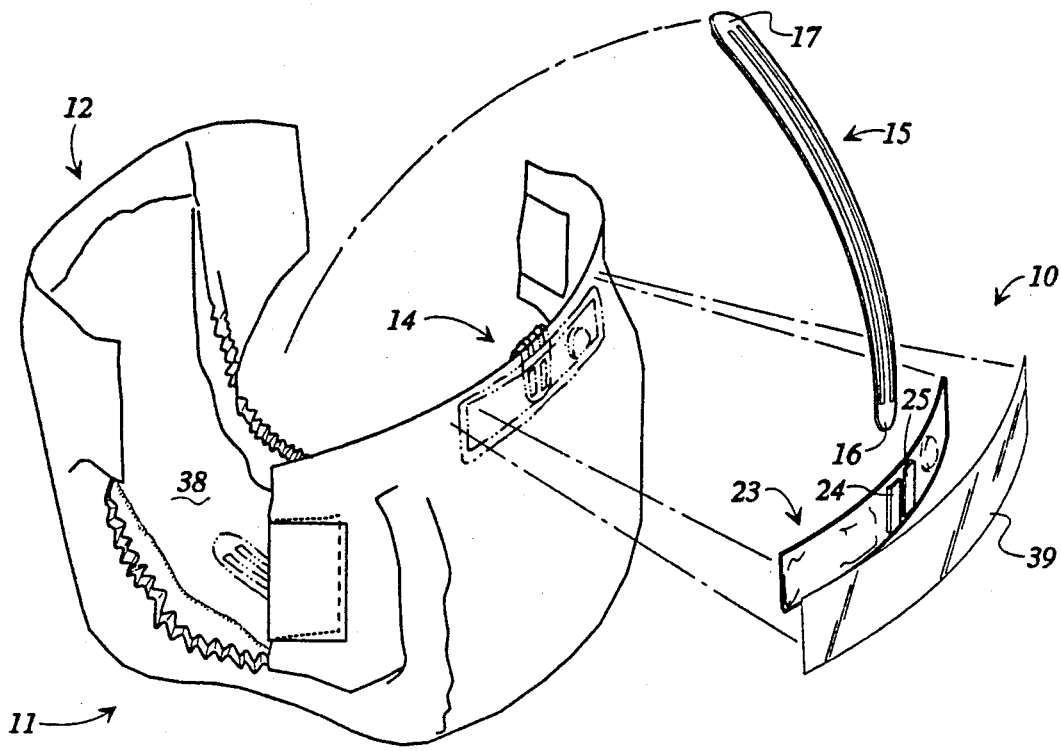
FIG. 1 is a perspective partially exploded view of a wet diaper detector that embodies principles of the present invention in one preferred form.

Referring now in more detail to the drawings, in which like numerals refer to like parts throughout the several views, FIG. 1 illustrates a wet diaper detector assembly 10 that embodies principles of the invention in one preferred form. The assembly 10 is shown partially exploded to reveal clearly the elements of the invention with the preferred placement of the assembly on a diaper 11 being illustrated in phantom lines.

Figure 2:
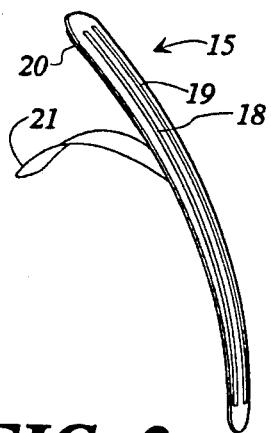
FIG. 2 is a detailed perspective view of the disposable conductor bearing strip of the invention.

The detector assembly 10 comprises an elongated strip of material 15, which has first and second ends 16 and 17 respectively. The strip 15 preferably is formed of a moisture absorbent insulating material and carries a pair of spaced conductors 18 and 19 (FIG. 2) that extend along the length of the strip 15. As illustrated in FIG. 2, the strip 15 is provided with an adhesive backing 20 that is normally protected by a peel-off strip 21. In use, the peel-off strip 21 is removed just prior to attaching the assembly 10 to a diaper so that the strip 15 can be adhered securely within the diaper extending through the crotch area thereof as illustrated in phantom lines in FIG. 1.

A generally rectangular flexible band 23 carries the electronic detector and alarm circuitry of the invention and is adapted to be positioned on the exterior of a diaper 11 at the upper front or rear portion 14 thereof. In use, the band 23 is releasably secured to the diaper by means of a rectangular adhesive patch 39 that is slightly larger than the band 23 and that is applied over the band to cover and protect it during use and to secure it releasably to the diaper's exterior surface.

Figure 3:
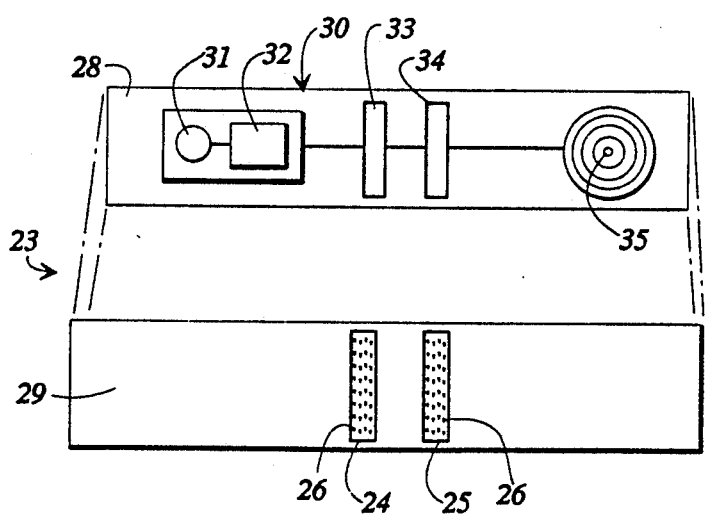
FIG. 3 is a partially exploded view showing a preferred construction of the rectangular component carrying band of the invention.

As best illustrated in FIG. 3, the flexible band 23 preferably is fabricated from two rectangular strips 28 and 29 of flexible material between which is sandwiched the miniaturized electronic components 30 of the invention. During assembly of the band, the rectangular strips 28 and 29 are adhesively and permanently joined to form a unitary sandwiched assembly such that the electronic components become sealed and protected between the strips 28 and 29.

The electronic components 30 and their configuration are discussed in detail hereinbelow. In general, however, these components comprise a power source in the form of a small thin battery 31 that powers a detector circuit 32 and an audible alarm 35, which, in the preferred embodiment, comprises a miniaturized melody source of the type commonly embedded within greeting cards and the like. A pair of spaced electrical contacts 33 and 34 are positioned in the mid-portion of the band 23 and are coupled to the detector 32. The detector 32 is configured to monitor the electrical resistance between the contacts 33 and 34 and to activate the alarm 35 when such resistance falls below a pre-established value.

The exterior surface of rectangular strip 29 carries a pair of spaced spiked or barbed conductive guides 24 and 25 positioned to overly and make electrical contact with the contacts 33 and 34 when the strips 28 and 29 are sandwiched together. The guides 24 and 25 are configured to receive and position the protruding end 16 of strip 15 at the mid-portion of band 23 as illustrated in FIG. 1. The spikes or barbs 26 penetrate the strip and make electrical contact between each of the guides 24 and 25 and a respective one of the conductors 18, 19 of the strip 15. It will thus be clear that, with the wet diaper detector thus assembled, the detector circuit monitors the electrical resistance between the spaced conductors of the strip 15.

When using the embodiment of FIGS. 1-3 for detecting and signaling a wet diaper condition, the elongated conductor bearing strip 15 is adhesively secured within a diaper extending through the crotch area thereof with one end 16 of the strip protruding from within the diaper at the upper edge 14 thereof. The detector band 23 is then pressed onto the strip end 16 with each conductor of the strip overlying a respective one of the barbed guides 24 and 25. The pressing of the strip end and band together causes the barbs 26 to penetrate the strip to establish reliable electrical contact between the guides 24 and 25 and the conductors 18 and 19.

With the strip end and band pressed together, the strip is folded over the top edge of the diaper to position the detector band on the outside of the diaper of the upper front or rear portion thereof as shown in phantom lines in FIG. 1. The band 23 and strip end 16 are then securely but releasably affixed to the diaper by means of the adhesive backed patch 39, which is sized to overly and cover the band to protect it from food, moisture, and unwanted tampering.

With the assembly 10 thus installed, the diaper is placed on an infant in the usual way and the detector circuit begins to monitor the resistance between the conductors 18 and 19 within the diaper. The pre-established resistance threshold value is selected such that the monitored resistance between the conductor is above the threshold when the diaper is dry but falls below the threshold when the diaper and the strip therein become wet. Accordingly, when the infant wets its diaper, the resulting resistance drop is detected by the detector, which, in turn, activates the alarm to alert a parent or attendant to the wet diaper condition. When the soiled diaper is changed, the detector band 23 is removed from the diaper and decoupled from the strip end 16 for reuse on a fresh diaper. The used conductor strip 15, which is inexpensive and thus expendable, is simply discarded with the soiled diaper.

FIGS. 4-6 illustrate a second or alternate embodiment 40 of the present invention. This embodiment is also configured for use with an ordinary diaper 41 that has front and rear portions 42 and 44 and an inner intermediate portion 45. The assembly 40 comprises an inverted T-shaped flexible strip 46 having an elongated first leg 48 and a second leg 49, which preferably extends normal to the first leg 48 (FIGS. 1 and 2). Extending along the length of the first leg 48 is a pair of spaced conductors 50 and 51, that terminate in respective contacts 53 and 54 at the intersection of the legs of the T-shaped strip 46.

Preferably, adhesive backings 55 and 56 are provided on the second leg 49 of the T-shaped strip 46 for purposes detailed below and the backings are normally protected by peel-off strips (not shown). Adhesive backing and a peel-off strip also is provided along the back side of leg 48 so that this leg can be secured within the interior of the diaper as detailed below. An adhesive backing 58 (FIG. 5) can also be provided on the back of the T-shaped strip 46 at the intersection of its legs for securing the wet diaper detector assembly 40 onto the exterior surface of the diaper 41 as illustrated in phantom lines in FIG. 4.

Figure 7:
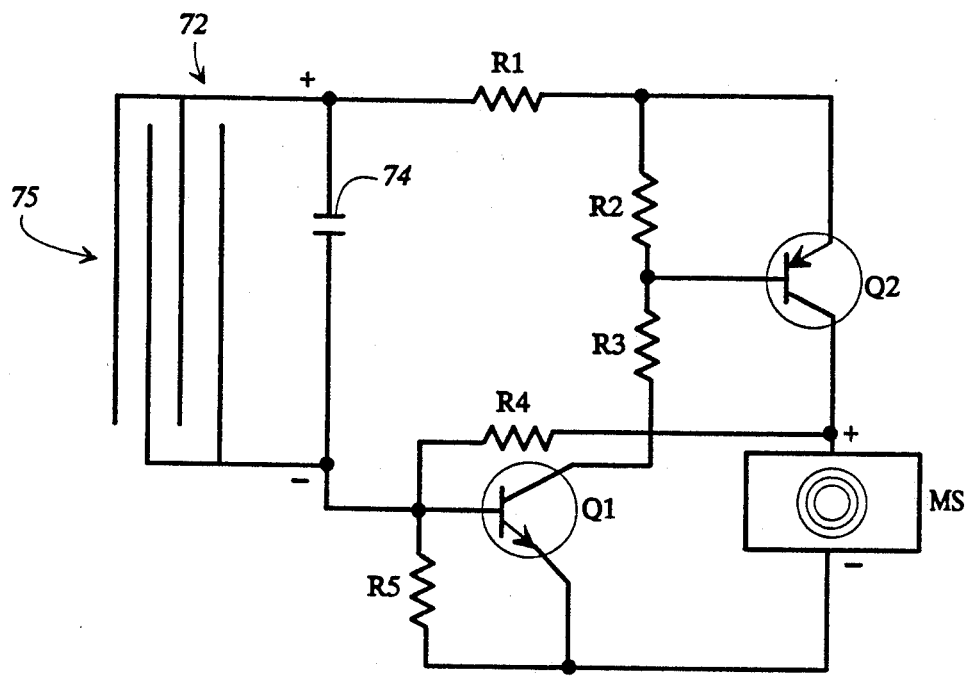
FIG. 7 is an electrical schematic diagram showing one preferred circuit for implementing the present invention.
Figure 8:
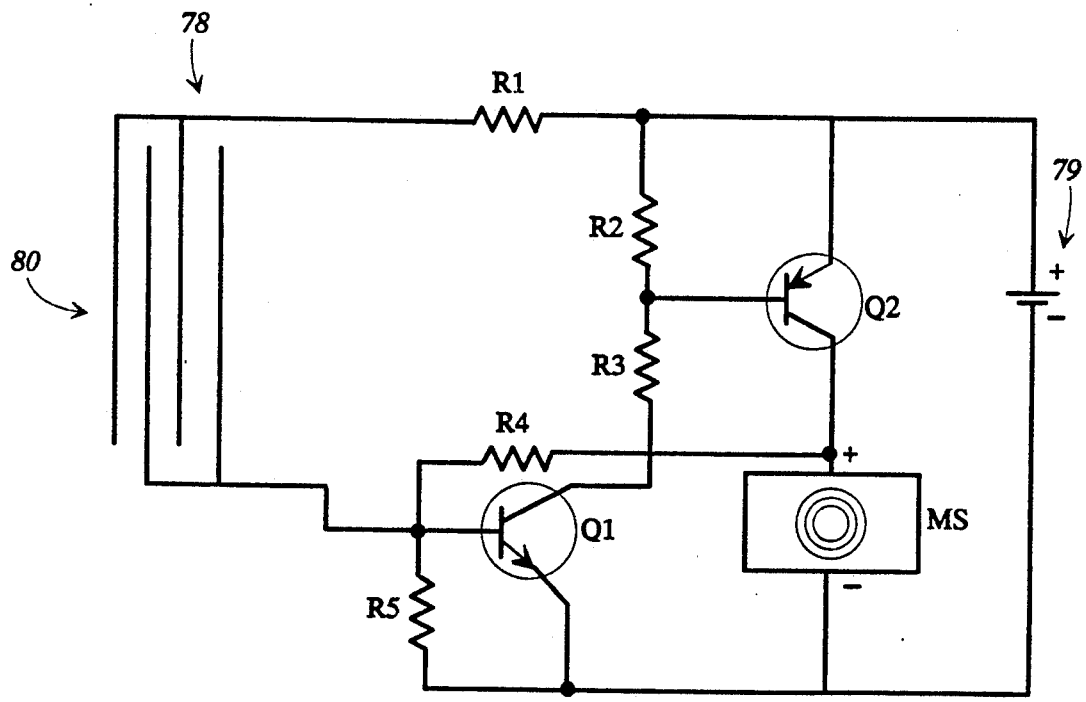
FIG. 8 is an electrical schematic diagram showing an alternate circuit for implementing the invention.

As illustrated in FIG. 6, a detector and alarm circuit is encased within a thin plastic housing 60 having a front side 61 (FIG. 4) and a rear side 62. A pair of spaced electrical contacts 64 and 65 are located on the rear side 62 of the housing 60 and are electrically coupled to the detector circuit within the housing, as discussed below and as illustrated in FIGS. 7 and 8.

The housing 60 encloses the miniaturized electrical circuitry that, as in the first embodiment, monitors the electrical resistance between the contacts 64 and 65 and activates the alarm when such resistance falls below a pre-established threshold value. The contacts 64 and 65 are spaced to overlay and make electrical contact with the contacts 53 and 54 on the T-shaped strip 46 when the housing 60 is pressed into position at the intersection of the legs of the strip as best seen in FIG. 4. It will be apparent that with the housing 60 thus positioned, the detector monitors the electrical resistance between the spaced conductive strips 50 and 51 that extend along leg 48 and activates the alarm when such resistance falls below the pre-established threshold value.

The wet diaper detector assembly 40 is shown in phantom lines in FIG. 4 as it appears when installed on a diaper 41 for use. When installing the assembly, the T-shaped strip 46 is first affixed to the outside rear or front portion 44 of the diaper by means of the adhesive backing 58 on the back side of the strip 46. The second leg 48 of the strip 40 is then folded over the top edge of and into the interior of the diaper, where it is adhesively secured in position extending through the crotch area of the diaper (FIG. 4). Thus, the conductive strips 50 and 51 are exposed within the diaper at its crotch portion, which tends to be the portion most susceptible to wetness.

With the first leg 48 of the T-shaped strip positioned in the diaper as shown at 70, the detector housing 60 is positioned at the intersection of the legs of the T-shaped strip with each of its contacts 64 and 65 engaging a respective one of the contacts 53 and 54 thus coupling the detector to the conductors 50 and 51. The protective peel-off strips are then removed from the adhesive backing 55 and 56 and the second leg 49 of the strip 46 is folded up and over the housing 60 and adhesively secured to the exterior of the diaper on either side of the housing. The housing 60 is thus securely captured and held in place by the folded and secured second leg 49 of the T-shaped strip 46 as illustrated in FIG. 4. With the detector assembly 40 thus secured, the diaper can be fitted to an infant or toddler in the normal way.

When the diaper 41 is fitted to the infant, the resistance between the two metal strips 50 and 51 normally remains above a threshold as long as the interior portion 45 of the diaper 41 is dry. However, when the infant wets his diaper, thus wetting the first leg 48 of the T-shaped strip 46 at 70, the resulting moisture causes the resistance between the conductors 50 and 51 to fall below the threshold level. The detector circuit detects this reduction in resistance and activates the alarm, which preferably emits a pleasant melody, to alert an adult or an attendant of the wet diaper condition. The wet diaper can then be changed, whereupon the detector housing 60 is removed for reuse while the used T-shaped strip 46 is discarded along with the soiled diaper.

FIG. 7 is an electronic schematic diagram illustrating a preferred circuit for implementing the present invention. In this embodiment, the spaced conductors 75, which normally are positioned on the strip within a diaper, are formed of dissimilar metals such as, for example, silver and copper. In this way, when acidic urine contacts the conductors the urine functions as an electrolyte and the conductors and urine become a battery that supplies power for operation of the circuit.

As the conductors 75 become charged upon contact with urine, they provide current to charge capacitor 74. When capacitor 74 becomes sufficiently charged, the electrical potential across the capacitor functions to "turn on" transistor Q1, which, in turn, conducts sufficient current through R1 and through voltage divider pair R2 and R3 to turn on transistor Q2. With transistor Q2 in its on or conducting state, power is supplied to the alarm MS, causing the alarm to emit an audible alert signal. Preferably, the alert signal is a pleasing melody that will not upset an infant but that will be sufficiently noticeable to alert a parent or guardian to the presence of wetness within the diaper. In some instances, sufficient current is supplied by the urine battery for continuous operation of the alarm. However, in some instances, the generated current is not sufficient and the alarm is sounded intermittently as the capacitor 74 charges and discharges.

FIG. 8 is an electronic schematic diagram illustrating another embodiment of a detector and alarm circuit for implementing the present invention. In this embodiment, the circuit is powered by an auxiliary battery 79. In operation, the electrical resistance between conductors 80 falls when the conductors are contacted with urine or other wetness in the diaper. In turn, current is conducted through resistor R5 and R1. The resulting voltage drop across resistor R5 turns transistor Q1 on, which, in turn, turns on transistor Q2 as with the embodiment of FIG. 7. With transistor Q2 in its on or conducting configuration, power is supplied to the alarm MS, which emits an audible signal to alert the attendant of the wet condition of the diaper. With this embodiment, the audible alarm sounds continuously until the wet diaper is changed since continuous power is supplied by the battery 69.

The invention has been disclosed and described herein in terms of preferred configurations and methodologies. However, it will be obvious to those of skill in the art that numerous variations of the illustrated embodiments could be implemented within the scope of the invention. For example, the audible alarm of the preferred embodiments might easily be replaced with a visual indicator, such as a flashing LED, or even a small transmitter for transmitting a radio signal to a remote receiver when the diaper becomes wet. Further, a wide variety of simple electronics in addition to those illustrated might be implemented to perform the same functions in an acceptable way.

Also, the invention has been illustrated in terms of monitoring an electrical resistance and detecting when such resistance falls below a pre-established threshold. However, characteristics other than electrical resistance might well be substituted for resistance in the preferred embodiments with comparable results. For example, inductance or capacitance between sensing elements may be monitored with changes therein signaling a wet diaper condition. When measuring capacitance, an alternating signal could be applied to the exterior of the diaper through a first capacitive plate and signals from the diaper detected through a second capacitive plate, the interior of the diaper acting as a dielectric between the two capacitive plates. When moisture appears in the diaper, the capacitance between the plates and thus the nature of the monitored signal would change. Such change could then trigger activation of the alarm to alert parents to the wet diaper condition.

These and other additions, deletions, and modifications might well be made to the exemplary embodiments illustrated herein without departing from the spirit and scope of the invention as set forth in the claims.

I claim:

1. An apparatus for use with a diaper to detect the occurrence of a wet condition in the diaper and produce an alarm signal in response to such detection, said apparatus comprising:

an elongated strip of substantially insulative material sized and configured to be secured within a diaper with a portion of said elongated strip located in a region of the diaper subject to wetness and with an end of said elongated strip protruding from the inside of the diaper;

a pair of spaced electrical conductors on said elongated strip of material, said conductors extending along the length and terminating at said protruding end of said elongated strip;

a detector and alarm assembly having a pair of conductive contacts, means for monitoring the electrical resistance between said pair of conductive contacts, and means for producing an alarm signal when the monitored electrical resistance falls below a pre-established value;

said detector and alarm assembly being configured to be releasably coupled to the protruding end portion of said elongated strip with each of said conductive contacts of said assembly engaging and making electrical contact with a corresponding one of said spaced electrical conductors on said elongated strip;

means for releasably fastening said apparatus to a diaper with which said apparatus is to be used; and said means for releasably fastening said apparatus to a diaper comprising an elongated flap on the protruding end of and extending transversely with respect to said elongated strip, said flap being sized and configured to fold over said detector and alarm assembly when said assembly is coupled to the protruding end of said strip, said flap being provided with adhesive means for securing said flap, when folded, to a diaper on either side of said detector and alarm assembly to capture said assembly securely between said flap and the diaper thereby hold the assembly firmly but releasably in place on the diaper;

whereby the electrical resistance between the pair of spaced conductors is monitored and an alarm signal produced when wetness within the diaper bridges the spaced conductors on the elongated strip causing the resistance therebetween to fall below the pre-established value.

2. The apparatus as claimed in claim 1 and wherein said elongated strip includes adhesive means thereon for securing the strip in position within a diaper in a region of the diaper subject to wetness.

3. The apparatus as claimed in claim 1 and wherein said detector and alarm means is housed within a rigid housing having an exterior surface and wherein said conductive contacts are disposed on the exterior surface of said housing.

4. An apparatus for use with a diaper to detect the occurrence of a wet condition in the diaper and produce an alarm signal in response to such detection, said apparatus comprising:

an elongated strip of substantially insulative material sized and configured to be secured within a diaper with a portion of said elongated strip located in a region of the diaper subject to wetness and with an end of said elongated strip protruding from the inside of the diaper, said elongated strip and said flap together forming a T-shaped configuration;

a pair of spaced electrical conductors on said elongated strip of material, said conductors extending along the length and terminating at said protruding end of said elongated strip;

a detector and alarm assembly having a pair of conductive contacts, means for monitoring the electrical resistance between said pair of conductive contacts, and means for producing an alarm signal when the monitored electrical resistance falls below a pre-established value;

said detector and alarm assembly being configured to be releasably coupled to the protruding end portion of said elongated strip with each of said conductive contacts of said assembly engaging and making electrical contact with a corresponding one of said spaced electrical conductors on said elongated strip;

means for releasably fastening said apparatus to a diaper with which said apparatus is to be used;

said means for releasably fastening said apparatus to a diaper comprising an elongated flap on the protruding end of and extending transversely with respect to said elongated strip, said flap being sized and configured to fold over said detector and alarm assembly when said assembly is coupled to the protruding end of said strip, said flap being provided with adhesive means for securing said flip, when folded, to a diaper on either side of said detector and alarm assembly to capture said assembly securely between said flap and the diaper thereby hold the assembly firmly by releasably in place on the diaper; and whereby the electrical resistance between the pair of spaced conductors is monitored and an alarm signal produced when wetness within the diaper bridges the spaced conductors on the elongated strip causing the resistance therebetween to fall below the pre-established value.

* * * * *